(12) United States Patent
Bornzin et al.

(10) Patent No.: US 11,642,540 B2
(45) Date of Patent: May 9, 2023

(54) IMPLANTABLE MEDICAL SYSTEMS AND METHODS FOR INTERCOSTAL LEAD IMPLANT

(71) Applicant: Pacesetter, Inc., Sylmar, CA (US)

(72) Inventors: Gene A. Bornzin, Santa Monica, CA (US); Zoltan Somogyi, Simi Valley, CA (US); Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 17/062,738

(22) Filed: Oct. 5, 2020

(65) Prior Publication Data

US 2022/0105353 A1 Apr. 7, 2022

(51) Int. Cl.
*A61N 1/375* (2006.01)
*A61N 1/39* (2006.01)
*A61N 1/05* (2006.01)

(52) U.S. Cl.
CPC ......... *A61N 1/39622* (2017.08); *A61N 1/059* (2013.01); *A61N 1/37512* (2017.08); *A61N 1/37518* (2017.08)

(58) Field of Classification Search
CPC ............... A61N 1/39622; A61N 1/059; A61N 1/37512; A61N 1/37518; A61N 1/0504
See application file for complete search history.

(56) References Cited

U.S. PATENT DOCUMENTS

| | | | |
|---|---|---|---|
| 4,276,882 A * | 7/1981 | Dickhudt | A61N 1/057 607/9 |
| 5,107,856 A * | 4/1992 | Kristiansen | A61N 1/057 128/DIG. 26 |
| 2009/0149902 A1* | 6/2009 | Kumar | A61N 1/0587 607/4 |
| 2017/0021159 A1* | 1/2017 | Reddy | A61B 17/0401 |
| 2019/0298991 A1* | 10/2019 | Bornzin | A61B 5/283 |

* cited by examiner

*Primary Examiner* — Eugene T Wu
(74) *Attorney, Agent, or Firm* — The Small Patent Law Group LLC; Dean D. Small

(57) ABSTRACT

An implantable lead includes a lead body, electrical conductors, and a lead anchor. The lead body includes an electrode segment configured to be positioned along a pericardial membrane of a heart and including a plurality of electrodes configured to at least one of sense electrical signals from the heart or deliver therapy to the heart. The electrical conductors extend through the lead body between distal and proximal ends of the lead body, and are configured to electrically couple the electrodes to a pulse generator. The lead anchor is configured to be secured to a chest wall. The electrical conductors extend through the lead anchor, and the electrode segment extends from the lead anchor to the pericardial membrane. The electrode segment includes a transition portion that is configured to extend a depth into a mediastinum and a contoured portion to extend alongside and curve about the pericardial membrane.

23 Claims, 9 Drawing Sheets

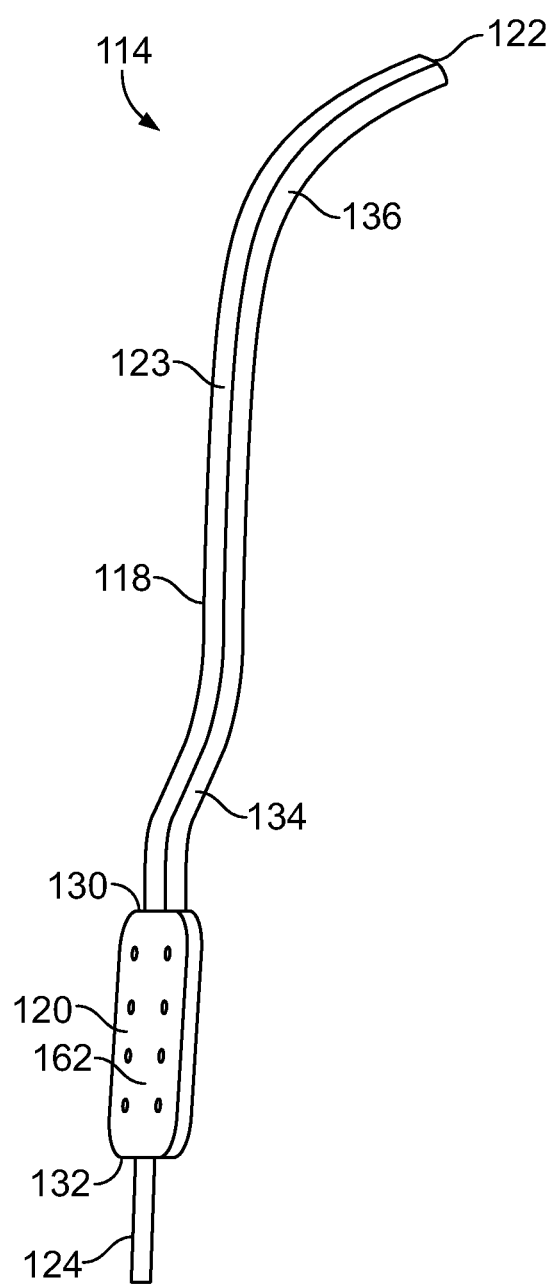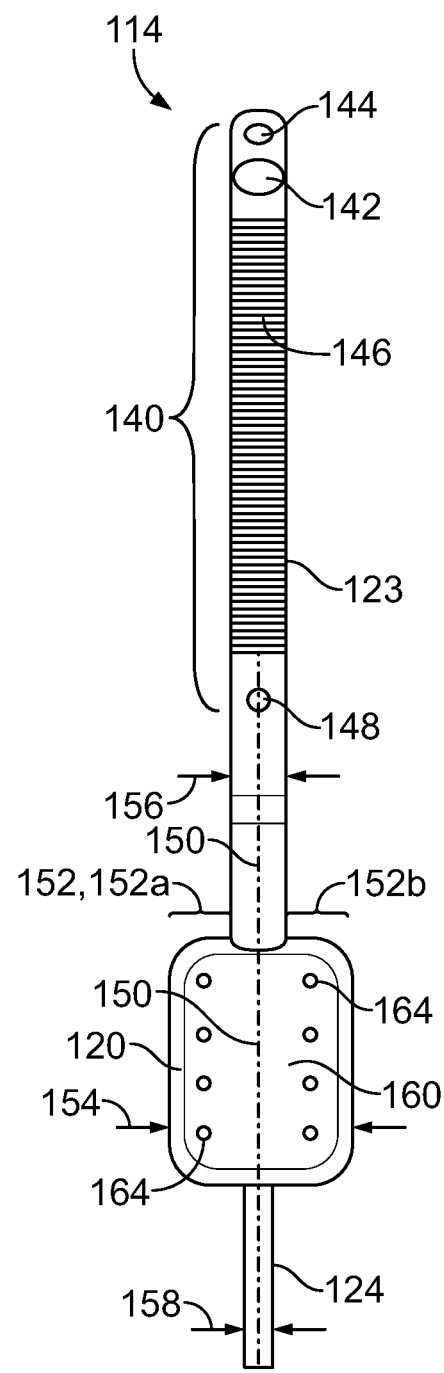
FIG. 3
FIG. 4

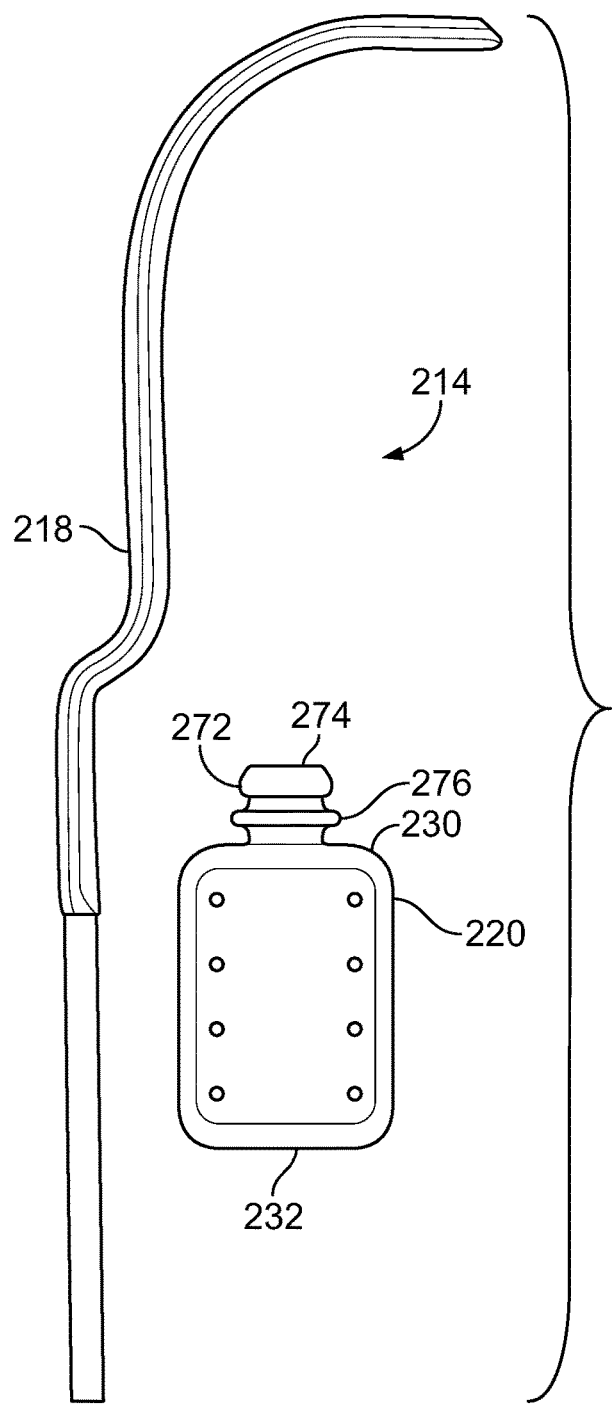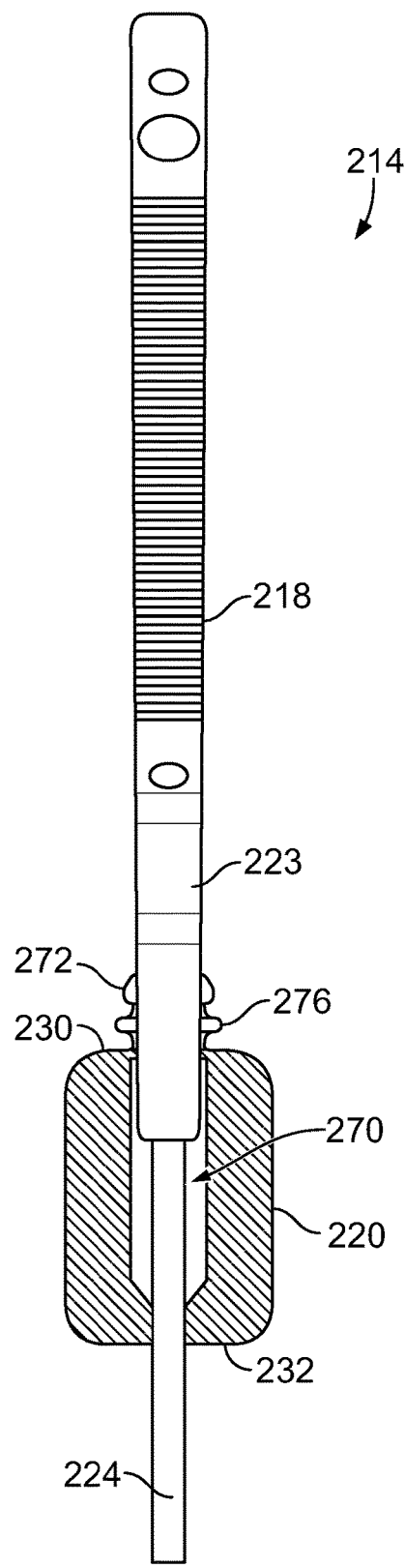
FIG. 6
FIG. 7

IMPLANTABLE MEDICAL SYSTEMS AND METHODS FOR INTERCOSTAL LEAD IMPLANT

BACKGROUND

Embodiments of the present disclosure relate generally to implantable medical devices and methods, and more particularly to medical devices having pulse generators and implanted leads.

Currently, implantable medical devices (IMD) are provided for a variety of cardiac applications. IMDs may include a "housing" or "canister" (or "can") and one or more electrically-conductive leads that connect to the housing through an electro-mechanical connection. IMDs contain electronics (e.g., a power source, microprocessor, capacitors, etc.) that control electrical activation of the leads to provide various functionalities. For instance, current IMDs may be configured for pacemaking, cardioversion, and/or defibrillation.

An implantable cardioverter-defibrillator (ICD) is one such medical device and it is designed to monitor heart rate, recognize certain events (e.g., ventricular fibrillation or ventricular tachycardia), and deliver electrical shock to reduce the risk of sudden cardiac death from these events. An ICD typically includes a pulse generator that is contained within a housing and one or more electrically-conductive leads that are controlled by the pulse generator. One conventional type of ICD uses transvenous leads in the right ventricle for detection and treatment of tachyarrhythmia. Although transvenous ICDs (or TV-ICDs) can prevent sudden cardiac death, TV-ICDs have certain drawbacks. For instance, obtaining venous access can be difficult and time-consuming, thereby prolonging the medical procedure. TV-ICDs are also associated with undesirable conditions or events, such as hemopericardium, hemothorax, pneumothorax, lead dislodgement, lead malfunction, device-related infection, and venous occlusion.

A second type of ICD, referred to as a subcutaneous ICD (or S-ICD), uses an electrode configuration that can reside entirely within the subcutaneous space, outside of the ribs and chest wall. Unlike the transvenous types, the S-ICDs lack intravenous and intracardiac leads and, as such, can be less likely to have the undesirable conditions or events associated with TV-ICDs. The S-ICD typically includes a shock coil that extends parallel to the sternum in a pectoral region of the patient. The shock coil is flanked by two sensing electrodes. The sensing electrodes sense the cardiac rhythm and the shock coil delivers countershocks through the subcutaneous tissue of the chest wall. Like the TV-ICD, conventional S-ICDs have been effective in reducing the incidence of sudden cardiac death. However, conventional S-ICD implantation uses three separate incisions: an axilla incision, an inferior parasternal incision near the xiphoid process, and a superior parasternal incision, and the risk of infection and other complications increases with each incision. Furthermore, S-ICD devices may require more power to deliver shocks than the TV-ICDs to achieve similar effect on the heart due to the greater distance between the subcutaneous leads and the heart.

Accordingly, a need remains for an IMD and implantation method that avoids the issues associated with the conventional TV-ICDs and S-ICDs described above, such as by requiring fewer incisions and limiting the amount of energy consumed for pacing, defibrillation, and/or other therapy to the heart.

SUMMARY

In accordance with embodiments herein, an implantable lead is provided that includes a lead body, electrical conductors, and a lead anchor. The lead body extends between distal and proximal ends. The lead body includes an electrode segment configured to be positioned along a pericardial membrane of a heart. The electrode segment includes a plurality of electrodes configured to at least one of sense electrical signals from the heart or deliver therapy to the heart. The electrical conductors extend through the lead body between the distal and proximal ends. The electrical conductors are configured to electrically couple the electrodes to a pulse generator. The lead anchor is configured to be secured to an anatomical structure of a chest wall. The electrical conductors extend through the lead anchor, and the electrode segment extends from the lead anchor to the pericardial membrane. The electrode segment includes a transition portion that is configured to extend a depth into a mediastinum and a contoured portion to extend alongside and curve about the pericardial membrane.

Optionally, the transition portion is disposed between the lead anchor and the contoured portion and at least one of the transition portion or the contoured portion is configured to bias the electrode segment against the pericardial membrane. Optionally, the contoured portion of the electrode segment is pre-formed to have a curved shape that follows a contour of the pericardial membrane. In an aspect, the transition portion of the electrode segment defines an S-shaped step-down configured to change the depth of the implantable lead from the anatomical structure of the chest wall to the pericardial membrane.

Optionally, the lead anchor is a discrete element with respect to the lead body and has an anchor passage. The lead body extends through the anchor passage. In an aspect, the lead body is slidable through the anchor passage to adjust a length that the electrode segment extends from the lead anchor. In an aspect, the lead anchor includes circumferential grooves surrounding the anchor passage. The grooves are configured to receive suture threads. Optionally, the lead body and the lead anchor are portions of a monolithic body.

Optionally, the lead anchor has at least one flanking portion that extends along the electrical conductors. An outer dimension of the implantable lead is greater along the at least one flanking portion of the lead anchor than along the electrode segment of the lead body. In an aspect, the at least one flanking portion has thru-holes to permit a suture thread to extend through the lead anchor. In an aspect, the at least one flanking portion includes opposite first and second flanking portions, and the lead anchor is paddle-shaped.

Optionally, the plurality of electrodes includes an anode and a cathode for at least one of pacing or bipolar sensing. The plurality of electrodes may also include an embedded elliptical coil for delivering electrical shocks.

In one or more embodiments, a computer implemented method for implanting an implantable medical device (IMD) is provided. The method includes inserting an elongated instrument through a chest wall of a patient to create an access opening to an intercostal space within the chest wall. The elongated instrument has a lumen. The method includes tunneling the elongated instrument along the intercostal space to create a passage from the access opening to a mediastinum of the patient. The method includes advancing a guidewire through the lumen of the elongated instrument and into the mediastinum, removing the elongated instrument, and advancing a dilator over the guidewire and through the intercostal space, thereby increasing a size of the access opening and a size of the passage through the intercostal space. The method also includes advancing an implantable lead through the access opening and the passage. The implantable lead has an electrode segment and a lead anchor. The method includes positioning the electrode segment alongside a pericardial membrane of the heart, and securing the lead anchor to an anatomical structure of the chest wall. The electrode segment extends from the lead anchor to the pericardial membrane. The electrode segment includes a transition portion that extends a depth into the mediastinum and a contoured portion that extends alongside and curves to follow a contour of the pericardial membrane.

Optionally, the implantable lead extends through the intercostal space of the chest wall. The transition portion may form a step-down which changes the depth of the implantable lead from the chest wall to the pericardial membrane. Optionally, advancing the implantable lead through the access opening and the passage includes rotating the implantable lead from a first orientation in which the contoured portion curves outward toward the chest wall to a second orientation in which the contoured portion curves inward toward the pericardial membrane. Positioning the electrode segment alongside the pericardial membrane of the heart may include sliding a lead body of the implantable lead through an anchor passage of the lead anchor to adjust a length that the electrode segment extends from the lead anchor.

Optionally, the method may also include shaping the electrode segment prior to advancing the implantable lead through the access opening. Optionally, positioning the electrode segment alongside the pericardial membrane of the heart may include positioning the electrode segment at least one of along or over the atrioventricular groove. Optionally, securing the lead anchor to the anatomical structure of the chest wall may include suturing the lead anchor to an adventitia of intercostal muscle.

Optionally, the method may also include implanting a pulse generator. The pulse generator may be implanted in a midaxillary region of the chest and electrically coupled to the implantable lead. Optionally, the pulse generator may be implanted adjacent to the lead anchor.

In one or more embodiments, an implantable medical system is provided that includes a pulse generator and a lead. The pulse generator is configured to be positioned within a patient. The pulse generator has a housing that includes an electronics module configured to at least one of analyze electrical signals of a heart or generate electrical signals for delivering therapy to the heart. The lead includes a lead body extending between distal and proximal ends. The lead body includes an electrode segment including a plurality of electrodes configured to at least one of sense the electrical signals from the heart or deliver the therapy to the heart. The lead also includes electrical conductors and a lead anchor. The electrical conductors extend through the lead body and electrically couple the electrodes to the pulse generator. The lead anchor is configured to be secured to an anatomical structure of a chest wall. The electrical conductors extend through the lead anchor, and the electrode segment extends from the lead anchor to a pericardial membrane of the heart. The electrode segment includes a transition portion that is configured to extend a depth into a mediastinum and a contoured portion to extend alongside and curve about the pericardial membrane.

BRIEF DESCRIPTION OF THE DRAWINGS

FIG. 3 is a side perspective view of an implantable lead in accordance with an embodiment.

FIG. 4 is a front view of the lead shown in FIG. 3.

FIG. 6 illustrates an implantable lead that includes a discrete lead body and lead anchor in accordance with an embodiment.

FIG. 7 illustrates a front view of the implantable lead in FIG. 6 showing the lead body mechanically coupled to the lead anchor.

DETAILED DESCRIPTION

Embodiments set forth herein include implantable medical devices (IMDs), systems that include IMD, and methods of using and positioning the same. The IMD implant techniques disclosed herein may require minimal surgical intervention. The IMDs disclosed herein may provide the same functions as conventional transvenous implantation systems, such as defibrillation and pacing therapies, without requiring transvenous implantation. For example, the IMDs may be implanted through intercostal spaces between ribs, and electrode segments of the IMDs may enter the mediastinum. The electrode segments may be placed on the pericardial membrane or pericardium of the heart to deliver therapy directly to the heart.

Furthermore, the features, structures, or characteristics described herein may be combined in any suitable manner in one or more embodiments. In this description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The description is intended only by way of example, and simply illustrates certain example embodiments.

Figure 1:
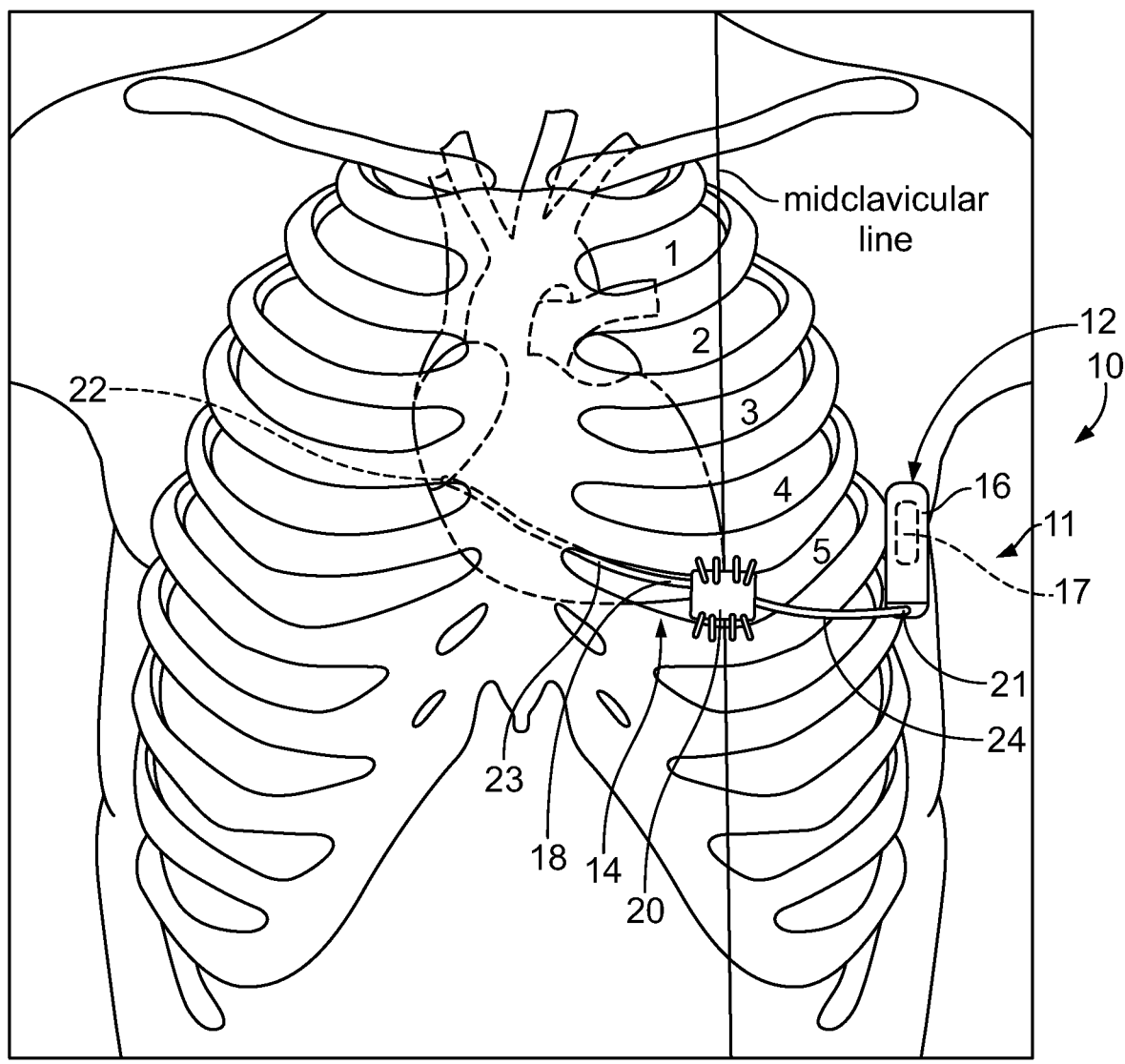
FIG. 1 illustrates an anterior view of a patient and an implantable medical system in the patient in accordance with an embodiment.

FIG. 1 illustrates an anterior view of a patient and an implantable medical system 10 in the patient in accordance with an embodiment. FIG. 1 illustrates the patient's torso and, in particular, the rib cage and the heart with the skin, muscle, fat, pericardium, and lungs omitted. The implantable medical system 10 includes an implantable medical device (IMD) 11. In particular embodiments, the IMD 11 may apply pacing therapy, cardiac resynchronization therapy (CRT), and/or general arrhythmia therapy, including defibrillation. For example, in at least one embodiment, the IMD 11 may have the capability to apply both pacing and defibrillation, when necessary. In a first alternative embodiment, the IMD 11 may provide pacing but not defibrillation. In a second alternative embodiment, the IMD 11 may provide defibrillation but not pacing.

The IMD 11 includes a header that is configured to be coupled to a lead 14. The lead 14 includes at least one electrode segment 23, including one or more electrodes, that is used for providing electrical shocks for pacing, defibrillation, and/or the like. For example, the IMD 11 may be configured to detect or sense cardiac activity (e.g., cardiac rhythm) via the lead 14, and to deliver various arrhythmia therapies via the lead 14, such as defibrillation therapy, pacing therapy, antitachycardia pacing therapy, cardioversion therapy, and the like, based on the cardiac activity. In the illustrated embodiment, the system 10 includes only the IMD 11, but the system 10 can include at least one additional component, such as a control device for programming the IMD 11.

The IMD 11 includes a housing or canister 16 that includes an electronics module 17 (shown in phantom in FIG. 1). The electronics module 17 is configured to analyze electrical signals of the heart and/or generate electrical signals for delivering therapy to the heart. The housing 16 may form or constitute a pulse-generator electrode, or alternatively may be connected to a discrete pulse-generator electrode (separate from the electrodes on the lead 14). In the illustrated embodiment, the IMD 11 is located in a midaxillary region of the chest of the patient. In other embodiments, the IMD 11 may be implanted in other areas of the patient's torso, such as the abdomen, sub-axillary region, or pectoral region. The IMD 11 may be subcutaneously implanted, such that the IMD 11 is disposed beneath the skin but above the chest wall which includes layers of skeletal muscle tissue, rib bones, and costal cartilage.

The lead 14 includes a lead body 18 and a lead anchor 20 connected to the lead body 18. The lead body 18 is elongated and extends from a proximal end 21 of the lead body 18 to a distal end 22 of the lead body 18. The proximal end 21 is mechanically and electrically connected to the IMD 11. For example, the proximal end 21 may include a connector that plugs into a port in the housing 16 of the IMD 11. The lead body 18 includes or represents an elongated tube or sleeve comprising, for example, a biocompatible material (e.g., polyurethane, silicone, etc.). The lead body 18 may include a single lumen (or passage) or multiple lumen (or passages) within the tube.

The lead body 18 includes an electrode segment 23 that is configured to be positioned along a pericardial membrane or pericardium of the heart. The electrode segment 23 includes a plurality of electrodes configured to sense electrical signals from the heart and/or deliver therapy to the heart. The electrode segment 23 extends from the lead anchor 20. The electrode segment 23 optionally may be referred to as a paddle, such as a defibrillation paddle. The lead body 18 also includes a cable segment 24 that extends from the electrode segment 23 to the IMD 11 and connects to the IMD 11. The lead 14 also includes a plurality of electrical conductors disposed within the lumen(s) of the lead body 18 that electrically couple the plurality of electrodes to the IMD 11. The electrical conductors may be cabled conductors coated with PTFE (poly-tetrafluoroethylene) and/or ETFE (ethylenetetrafluoroethylene). For example, the conductors may be terminated to respective electrodes of the electrode segment 23.

The lead anchor 20 secures to an anatomical structure of the chest wall of the patient. The electrode segment 23 of the lead body 18 extends from the lead anchor 20 to the pericardial membrane of the heart. Securing the lead anchor 20 to the chest wall holds the electrode segment 23 in position against or at least alongside the pericardial membrane. The electrode segment 23 may not be directly secured to the patient.

The lead 14 is designed for intercostal implant into the mediastinum of the chest. In FIG. 1, the intercostal spaces between the left ribs are labeled 1-5. The lead 14 in FIG. 1 is implanted through the $5^{th}$ intercostal space, which overlaps the left region of the heart. The lead anchor 20 is secured to the chest wall at the $5^{th}$ intercostal space, such as by suturing the lead anchor 20 to tissue. In a non-limited example, the lead anchor 20 may be sutured to an adventitia of intercostal muscle. The lead anchor 20 is aligned with a vertical midclavicular line in FIG. 1 (e.g., extending vertically along a plane that intersects a mid-point of the clavicle), but can be disposed in other locations in other embodiments. Alternatively, the lead 14 may be implantable through another intercostal space, such as the $4^{th}$ intercostal space which also extends over the left region of the heart.

As described in more detail herein, the lead body 18 is shaped to enable the electrode segment 23 to extend a depth from the lead anchor 20 at the chest wall into the mediastinum. A distal portion of the electrode segment 23 is disposed underneath the sternum, and is shown in phantom. In an embodiment, the lead 14 crosses a mid-sternal line that extends through a center of the sternum. The cable segment 24 of the lead body 18 extends from the electrode segment 23 and the lead anchor 20 to the IMD 11, which is shown in the midaxillary region of the chest in FIG. 1. It is notes that the IMD 11 in FIG. 1 provides a lead 14 with direct access to the pericardial membrane of the heart via intercostal implantation without insertion of a transvenous lead.

Figure 2:
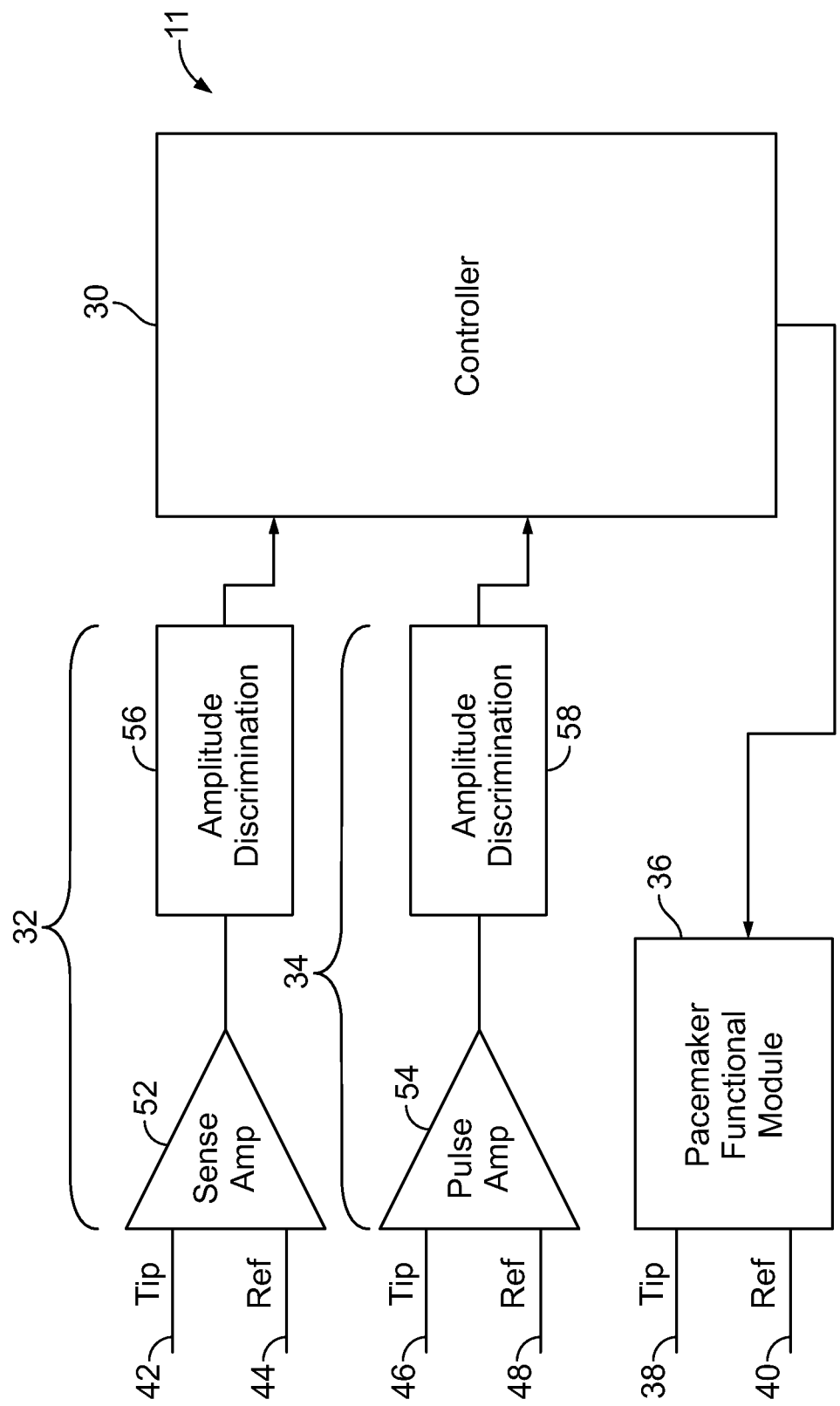
FIG. 2 illustrates a block diagram of at least a portion of the circuitry within an implantable medical device (IMD) in accordance with an embodiment herein that may be used with the system of FIG. 1.

FIG. 2 illustrates a simple block diagram of at least a portion of the circuitry within the IMD 11. The IMD 11 includes a controller 30 that may be coupled to cardiac sensing circuitry 32 and pulse sensing circuitry 34. The controller 30 also utilizes or communicates with various other electronic components, firmware, software, and the like that generally perform sensing and pacing functions (as generally denoted by a pacemaker functional block 36). While the examples herein are provided for pacing and defibrillation functions, the SIMD could be programmed to perform anti-tachycardia pacing, cardiac rhythm therapy, and the like. The cardiac sensing circuitry 32 is configured to detect one or more cardiac events (e.g., ventricular fibrillation, ventricular tachycardia, or other arrhythmia). The pulse sensing circuitry 34 is configured to detect event markers.

The controller 30 is configured to analyze incoming paced cardiac events (as sensed over the cardiac sensing circuitry 32). Based on this analysis, the controller 30 in the IMD 11 may perform various pacemaker related actions, such as setting or ending timers, recording data, delivery of therapy, and the like. The controller 30 of the IMD 11 may also perform various cardioversion/defibrillation related functions. In the example of FIG. 2, outputs 38 and 40 represent output terminals that are coupled through a switching circuit (in the functional module 36) to corresponding electrodes on the housing of the IMD 11. Alternatively, one or both of the outputs 38 and 40 may be coupled to the electrode segment 23 along the lead 14 (FIG. 1).

Inputs 42, 44, 46, 48 are provided to the cardiac and pulse sensing circuitry 32 and 34. By way of example, with reference to IMD 11, inputs 42 and 44 may be coupled to sensing electrodes along the electrode segment 23 that supply sensed signals to a sensing amplifier 52. Inputs 46 and 48 may be coupled to the same or different sensing electrodes to provide sensed signals to a pulse amplifier 54. An output of the sensing amplifier 52 is supplied to amplitude discriminator 56, while an output of the pulse amplifier 54 is supplied to amplitude discriminator 58. Outputs of the amplitude discriminators 56 and 58 are then provided to the controller 30 for subsequent analysis and appropriate actions. The inputs 42 and 44 may be coupled to various combinations of the electrode segments 22, 24 or the PG housing 16.

FIG. 3 is a side perspective view of an implantable lead 114 according to an embodiment. The implantable lead 114 (also referred to herein simply as lead 114) may have components that are the same as or similar to the lead 14 of the IMD 11 shown in FIG. 1. For example, the lead 114 includes a lead body 118 and a lead anchor 120. The lead body 118 includes an electrode segment 123 and a cable segment 124. The electrode segment 123 extends from a first edge 130 of the lead anchor 120 to a distal end 122 of the lead body 118. In the illustrated embodiment, the cable segment 124 extends from a second edge 132 of the lead anchor 120 that is opposite first edge 130. The cable segment 124 connects to the header of the IMD 11.

The electrode segment 123 has a non-linear, contoured shape. The electrode segment 123 includes a transition portion 134 and a contoured portion 136. The transition portion 134 is shaped for enabling the electrode segment 123 to extend a depth into the mediastinum through an intercostal space in the chest wall. For example, the transition portion 134 forms a step-down that abruptly changes the depth of the lead 114 in the chest region from the depth of the secured lead anchor 120 to the depth of the distal end 122 of the electrode segment 123 in the mediastinum. The transition portion 134 may define an S-shaped curve that transitions, in a depth direction, from a plane generally extending along an exterior of the ribs to a plane that extends along an interior of the ribs. The transition from the exterior to the interior of the ribs occurs along a lateral direction over a short distance, such as a few centimeters or a width of 1-3 ribs. The contoured portion 136 is shaped for following a contour of the pericardial membrane of the heart. For example, when the lead 114 is secured in place in the patient, the contoured portion 136 extends alongside and curves about the pericardial membrane. The contoured portion 136 define a C-shape curve. The transition portion 134 is disposed between the lead anchor 120 and the contoured portion 136 along the length of the lead body 118.

In an embodiment, the electrode segment 123 is preformed to include the transition portion 134 and the contoured portion 136 such that the lead 114 is produced and shipped with the transition and contoured portions 134, 136 present. In one non-limiting example, the transition and contoured portions 134, 136 may be formed during a molding process as the lead 114 is manufactured. The shape of the electrode segment 123 may be defined in a mold. In another non-limiting example, the electrode segment 123 may include a shape memory alloy, such as a nitinol wire skeleton, embedded within the polymer material of the lead body 118. In other non-limiting examples, a heat-treated coil may be embedded within the polymer material, and the coil may be flexible until a heat treatment causes the shape of the coil to set. In an alternative embodiment, the lead body 118, or at least the electrode segment 123 thereof, is a flexible and not pre-formed to include the illustrated contours. For example, a medical professional may bend and shape the electrode segment 123 after receiving the IMD and prior to implanting the IMD in the patient.

FIG. 4 is a front view of the lead 114 according to an embodiment. The front of the lead 114 is the side that faces the heart when in a final implanted position in the patient. The electrode segment 123 includes a plurality of electrodes 140 configured for sensing electrical signals and/or delivering therapy to the heart. The electrodes 140 include an anode 142 and a cathode 144 for bipolar sensing and/or pacing (e.g., delivering pacing therapy). The cathode 144 may be a hemispherical protrusion for physically engaging the pericardial membrane of the heart. In the illustrated embodiment, the lead 114 is designed for both pacing and defibrillation. For example, the electrode segment 123 also includes an elliptical coil 146 for delivering electrical shocks during defibrillation and/or cardioversion events. The electrical shocks delivered by the coil 146 for defibrillation may have higher power (e.g., voltage and/or current) than the electrical pulses provided by the cathode 144 and/or anode 142 for pacing. The coil 146 may be embedded within the polymer material of the lead body 118. In the illustrated embodiment, the anode 142 and the cathode 144 are both distal of the elliptical coil 146. The electrode segment 123 optionally also includes an electrode 148 that is disposed between the elliptical coil 146 and the lead anchor 120 along the length of the lead body 118, such that the coil 146 is between the electrode 148 and the set of electrodes 142, 144.

The lead 114 includes electrical conductors 150 that extend along the length of the lead body 118 within an interior of the lead body 118. The conductors 150 are represented by a dashed line in FIG. 4. The conductors 150 electrically couple (e.g., conductively connect) the electrodes 140, including electrodes 142, 144, 148 and coil 146, to the pulse generator of the IMD 11. The conductors 150 extend through the lead anchor 120.

The lead anchor 120 has at least one flanking portion 152 that extends along a side of the electrical conductors 150. Due to the at least one flanking portion 152, an outer dimension, such as a width, of the lead 114 is greater along the lead anchor 120 than along the lead body 118. For example, a width 154 of the lead anchor 120 is greater than a width 156 of the electrode segment 123 and a width 158 of the cable segment 124. In the illustrated embodiment, the lead anchor 120 includes a first flanking portion 152A and a second flanking portion 152B that extend along opposite sides of the conductors 150. The lead anchor 120 may be paddle-shaped, with opposite front and rear planar sides 160, 162. Only the front planar side 160 of the lead anchor 120 is shown in FIG. 4, and the rear planar side 162 is shown in FIG. 3. The lead anchor 120 is designed to be secured to an anatomical structure of the chest wall. In the illustrated embodiment, the lead anchor 120 defines thru-holes 164 along the flanking portions 152A, 152B. Each thru-hole 164 permits a suture thread to extend through the lead anchor 120. The thru-holes 164 may be defined in only one of the flanking portions 152A, 152B in an alternative embodiment. In another alternative embodiment, the lead anchor 120 does not have pre-defined thru-holes. For example, the composition of the lead anchor 120 may be a pierceable material such that a needle attached to suture thread can penetrate the lead anchor 120 to effectively form thru-holes.

In the illustrated embodiment, the lead body 118 (including the electrode segment 123 and the cable segment 124) and the lead anchor 120 are portions of a monolithic (i.e., one-piece) body. The lead body 118 may be seamlessly connected to the lead anchor 120. For example, the lead body 118 may be integrally formed with the lead anchor 120 during a common production process, such as molding operation, or may be separately formed but subsequently integrally connected via chemical bonding, such as in the presence of heat.

Figure 5:
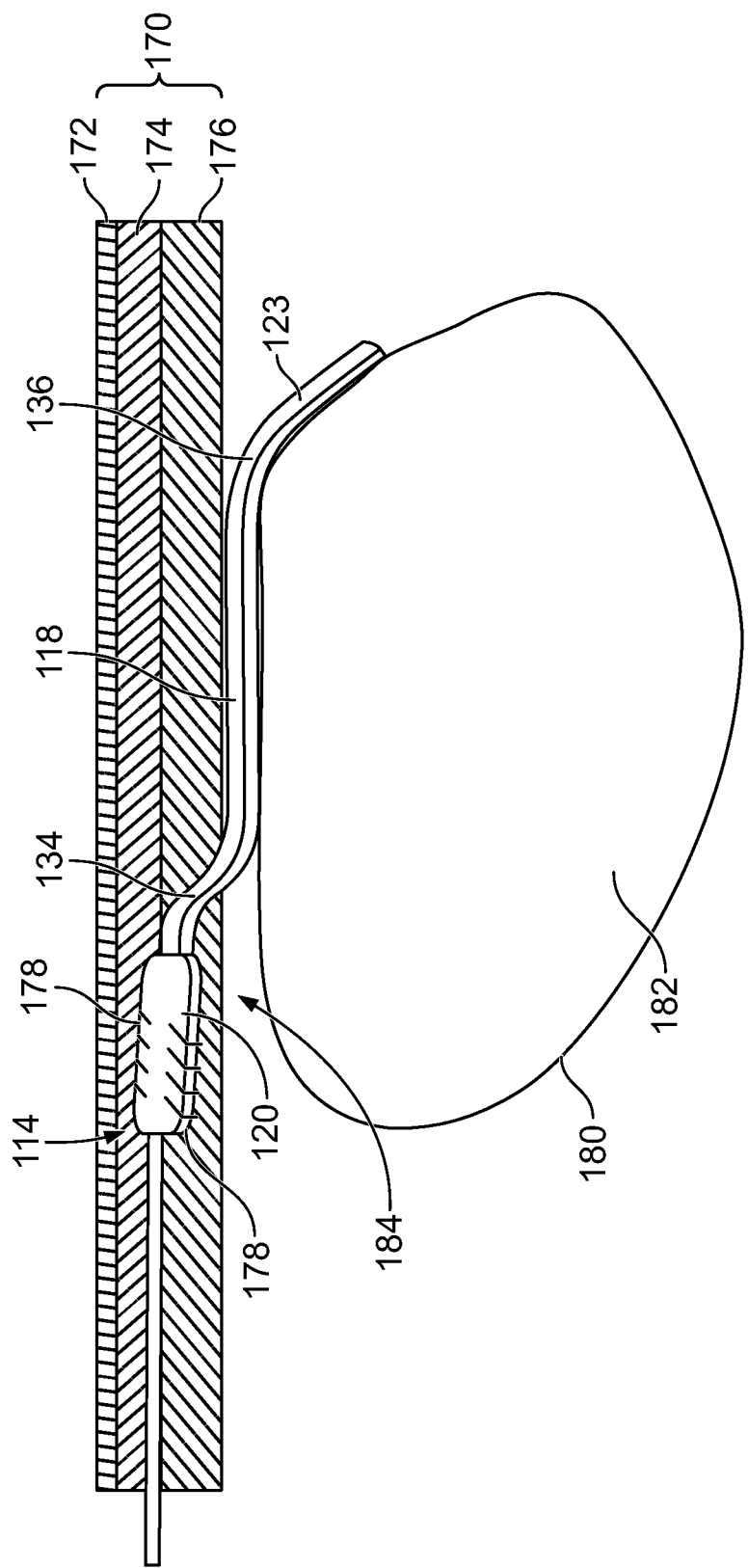
FIG. 5 is a sectional view of the implantable lead in FIGS. 3 and 4 when fully implanted in a patient in accordance with an embodiment.

FIG. 5 is a sectional view of the implantable lead 114 when fully implanted in a patient according to an embodiment. The lead anchor 120 of the lead 114 is secured to a chest wall 170 of the patient, which is shown in cross-section. For example, the lead anchor 120 is (subcutaneously) disposed under the skin 172 within a fat layer 174 and/or a muscular fascia layer 176. Sutures 178 extend through the lead anchor 120 to secure the lead anchor 120 to the muscular fascia layer 176. Securing the lead anchor 120 to the chest wall 170 holds the electrode segment 123 of the lead body 118 in a desired position alongside the pericardial membrane 180 of the heart 182. Although lead anchor 120 is secured to the muscular fascia in FIG. 5, the lead anchor 120 may be secured to other anatomical structures of the chest wall of the patient instead of, or in addition to the muscular fascia, in other embodiments. Such other anatomical structures can include bone, the fat 174, and other connective tissues.

The transition portion 134 has the S-shaped, step-down that abruptly changes the depth of the lead 114 from the anatomical structure of the chest wall 170 (to which the lead anchor 120 is secured) to the mediastinum 184 of the patient underneath the chest wall 170. For example, the length of the lead body 118 distal of the transition portion 134 is disposed below (e.g., deeper than) the chest wall 170 within the mediastinum 184. The shape and/or size of the transition portion 134 can be varied based on the size of the patient, such that smaller patients may require less of a step-down in depth than larger patients. The shape and/or size of the transition portion 134 can also be varied based on which anatomical structure the lead anchor 120 is secured to, as the step-down may be less for anatomical structures disposed closer to the pericardial membrane 180 than anatomical structures disposed farther from the pericardial membrane 180.

The contoured portion 136 of the electrode segment 123 is disposed in the mediastinum 184 and extends alongside the pericardial membrane 180. The contoured portion 136 is curved to follow the contour of the heart 182, or at least the contour of the pericardial membrane 180 surrounding the heart 182. In a non-limiting example, the lead 114 may be positioned such that the contoured portion 136 curves along the right ventricle over (or along) the atrioventricular (A-V) groove to the right atrial surface. The electrode segment 123 may physically contact (e.g., abut against) the pericardial membrane 180. For example, the transition portion 134 and/or the contoured portion 136 may bias the electrode segment 123 against the pericardial membrane 180. As the heart beats, the heart may repeatedly push the electrode segment 123 outward away from the heart, but the electrode segment 123 resiliently returns towards the heart to maintain the desired proximity to the pericardial membrane 180. The biasing force may be sufficiently minor to avoid causing the electrode segment 123 to obstruct the working movements of the heart. Alternatively, the lead 114 may be positioned such that the electrode segment 123 extends alongside and follows the contour of the pericardial membrane 180 without physically contacting the pericardial membrane 180. For example, the electrode segment 123 may retain a designated proximity range from the pericardial membrane 180, such as 2 mm, 5 mm, 10 mm, or the like, along the length of the electrode segment 123. By achieving the position of the electrode segment 123 shown in FIG. 5, there is very limited distance, if any, between the electrodes 142, 144, 146, 148 shown in FIG. 4 and the pericardial membrane 180 which allows for accurate sensing of electrical signals from the heart 182 and energy-efficient pacing pulses and defibrillation shocks.

FIG. 6 illustrates an implantable lead 214 that includes a discrete lead body 218 and lead anchor 220 according to an embodiment. The lead 214 is similar to the lead 114 shown in FIGS. 3 through 5 except for a few notable differences. For example, the lead anchor 220 is a discrete element with respect to the lead body 218. The lead body 220 is mechanically separated and spaced apart from the lead body 218 in FIG. 6. FIG. 7 illustrates a front view of the implantable lead 214 showing the lead body 218 mechanically coupled to the lead anchor 220 according to an embodiment. The lead anchor 220 is a sleeve that defines an anchor passage 270. The lead anchor 220 is shown in cross-section in FIG. 7 to show the anchor passage 270. The lead 214 is adjustable.

The anchor passage 270 extends through an entire length of the lead anchor 220 and is open at both a first edge 230 and an opposite second edge 232 of the lead anchor 220. The lead body 218 extends through the lead passage 270. In the illustrated embodiment, the electrode segment 223 projects beyond the first edge 230 of the lead anchor 220, and the connector segment 224 projects beyond the second edge 232. The lead body 218 may be slidable through the anchor passage 270 to adjust a length that the electrode segment 223 extends from the lead anchor 220.

The lead anchor 220 includes a neck 272 that projects beyond the first edge 230. The anchor passage 270 continuously extends through the neck 272 and is open at a top end 274 of the neck 272. The neck 272 includes circumferential (e.g., annular) grooves 276 that surround the anchor passage 270. The grooves 276 are disposed along an exterior of the neck 272. The grooves 276 may be used to secure the lead body 218 in a fixed position relative to the lead anchor 220. For example, the grooves 276 may be configured to receive suture threads that wrap around the neck 272. Tightening the suture threads with the lead body 218 disposed in the anchor passage 270 may compress the neck 272 of the lead anchor 220 to hold or grip the lead body 218. Compressing the neck 272 to grip the lead body 218 may prohibit additional sliding of the lead body 218 relative to the lead anchor 220. For example, the lead body 218 may be slid through the anchor passage 270 until a desired length of the electrode segment 223 projects from the lead anchor 220, and then the suture threads are tightened to secure the lead body 218 to the lead anchor 220 in the desired position. In an alternative embodiment, the lead anchor 220 may lack the neck 272, and circumferential grooves may be defined along a perimeter of the flat paddle of the lead anchor 220. In another alternative embodiment, the lead anchor 220 may lack circumferential grooves, and instead may grip the lead body 218 via an interference fit, an adhesive, or heat shrinking of a polymeric material of the lead anchor 220.

Figure 8:
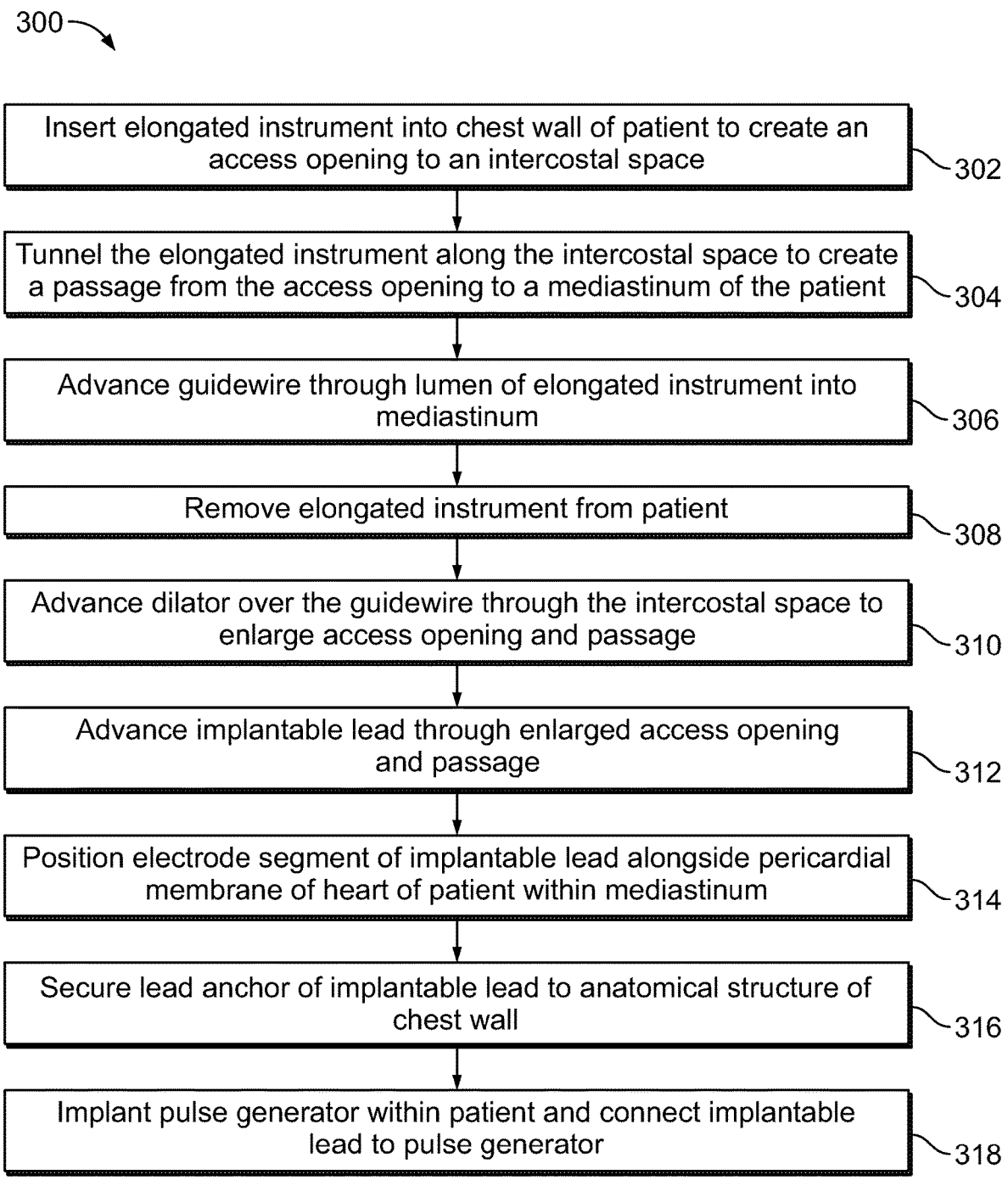
FIG. 8 is a flow chart of a method for implanting an IMD in accordance with an embodiment.

FIG. 8 is a flow chart of a method 300 for implanting an IMD, such as the IMD 11 in FIG. 1, according to an embodiment. The method 300 is described with reference to FIGS. 1 through 7. For example, references to an implantable lead may refer to the lead 14 shown in FIG. 1, the lead 114 shown in FIGS. 3 through 5, and/or the lead 214 shown in FIGS. 6 and 7. The method can be used for gaining access to the mediastinum of a patient without making a conventional surgical incision.

Figure 9:
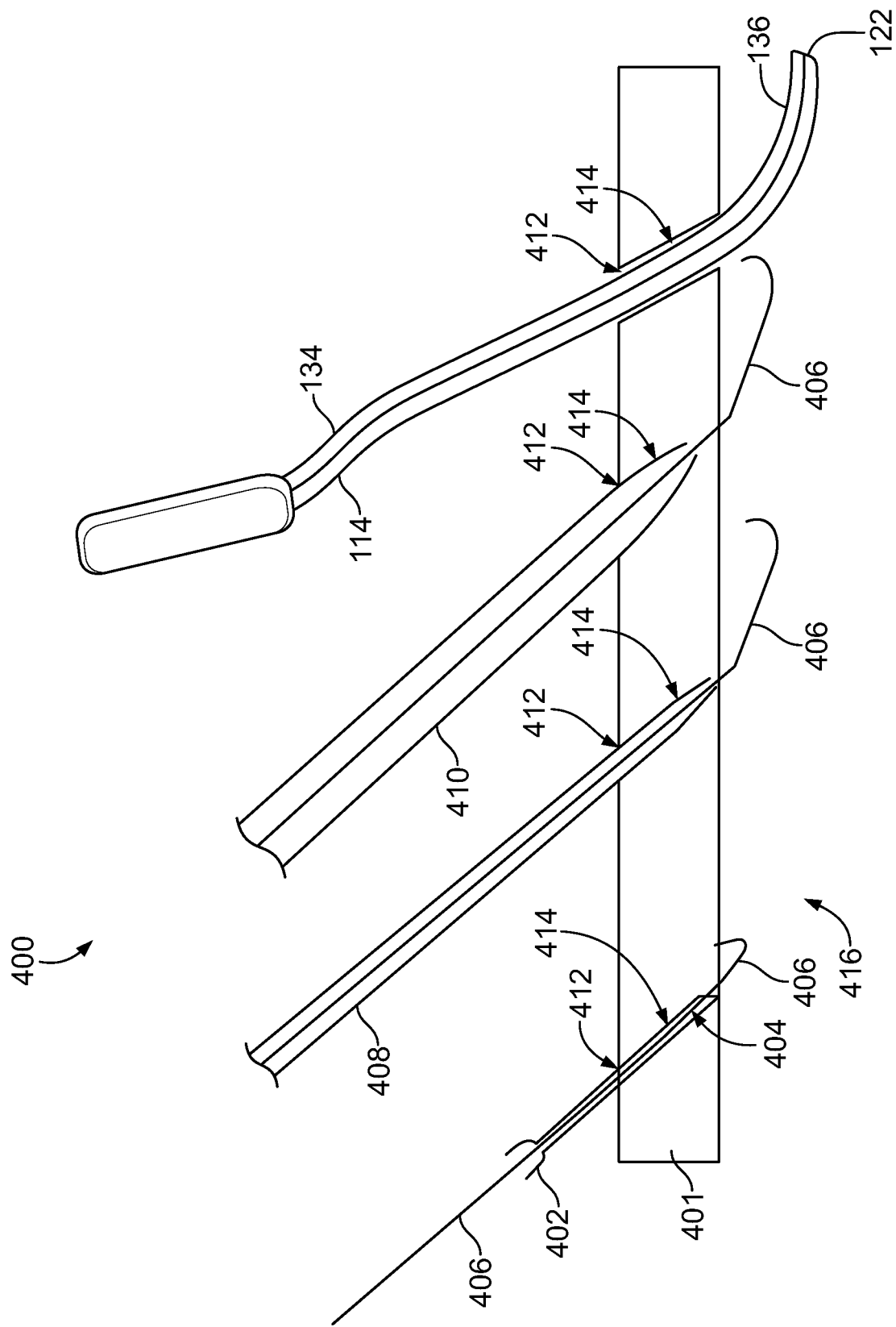
FIG. 9 shows components of a delivery system that may be used for implanting the IMDs according to the embodiments described herein.

The method 300 is also described with reference to FIG. 9, which shows components of a delivery system 400 that may be used for implanting the IMD according to the embodiments described herein. FIG. 9 includes FIGS. 9A, 9B, 9C, and 9D which show different components penetrating a chest wall 401. Each of the different FIGS. 9A-9D represents the same location at different times or stages in the implantation process, such that the components in FIG. 9B penetrates the chest wall 401 at the same location/opening as the components shown in FIG. 9A. FIG. 9A shows an elongated instrument 402 that has a lumen 404. The elongated instrument 402 may be a needle. A J-tip guidewire 406 is extends through the lumen 404. FIG. 9B shows a first dilator 408, and FIG. 9C shows a second dilator 410 that has a larger size (e.g., diameter) than the first dilator 408. FIG. 9D shows the lead 114.

Referring now to the method 300 in FIG. 8 and FIG. 9A, at 302, the elongated instrument 402 is inserted through the chest wall 401 to create an access opening 412 to an intercostal space (e.g., between two ribs) within the chest wall 401. Then, at 304, the elongated instrument 402 is tunneled along the intercostal space to create a passage 414 from the access opening 412 to a mediastinum 416 of the patient. At 306, the guidewire 406 is advanced through the lumen 404 of the elongated instrument 402 and into the mediastinum 416. At 308, the elongated instrument 402 is removed from the patient, without removing the guidewire 406.

At 310, and FIG. 9B, the first dilator 408 is advanced over the guidewire 406 and through the intercostal space. The first dilator 408 has a larger diameter than the elongated instrument 402, so inserting the first dilator 408 through the access opening 412 into the passage 414 increases the respective sizes of the access opening 412 and the passage 414. The first dilator 408 is then removed from the patient. Optionally, the second, larger dilator 410 can then be advanced over the guidewire 406 to further enlarge the access opening 412 and the passage 414. The process of sequentially inserting larger dilators can be repeated until the access opening 412 and passage 414 are sufficiently large to accommodate the lead 114. Then, the guidewire 406 is removed from the patient.

At 312, and FIG. 9D, the implantable lead 114 is advanced through the access opening 412 and the passage 414, such that the lead 114 extends through the intercostal space of the chest wall 401. As described above, the lead 114 includes a lead body 118 and a lead anchor 120. The lead body 118 has an electrode segment 123 that includes a plurality of electrodes. The electrode segment 123 includes a transition portion 134 and a contoured portion 136. As shown in FIG. 9D, the distal end 122 of the electrode segment 123 is inserted first through the access opening 412 and the passage 414, and then enters the mediastinum 416. Optionally, the lead 114 is initially advanced in a first orientation that is shown in FIG. 9D, in which the contoured portion 136, in the mediastinum 416, curves outward toward the chest wall 401. The advancing of the lead 114 may include rotating the implantable lead from the first orientation to a second orientation before the lead 114 is fully loaded into the passage 414. The second orientation is shown in FIG. 5, and the contoured portion 136 curves inward toward the pericardial membrane of the heart. The lead 114 may be rotated approximately 180 degrees (e.g., +/−30 degrees) from the first orientation to the second orientation.

At 314, the electrode segment 123 of the lead 114 is positioned alongside a pericardial membrane (or pericardium) of the heart. The electrode segment 123 can be positioned alongside the pericardial membrane due to the transition portion 134, which extends a depth into the mediastinum 416. For example, the transition portion 134 forms a step-down which abruptly changes the depth of the lead 114 from the chest wall 401 to the pericardial membrane, as shown in FIG. 5. In addition, the contoured portion 136 is specifically shaped to extend alongside and curve to follow a contour of the pericardial membrane. The electrode segment 123 may be positioned to extend along and/or over the atrioventricular groove of the heart. According to embodiments described herein, the electrode segment 123 is shaped to include the non-linear contours and curves prior to advancing the lead 114 through the access opening 412 in the chest wall 401.

Optionally, with reference to FIGS. 6 and 7, the lead 214 may have a two-piece construction. Positioning the electrode segment 223 may include sliding the lead body 218 through an anchor passage 270 of the lead anchor 220 to adjust a length that the electrode segment 223 extends from the lead anchor 220.

At 316, the lead anchor 120 of the lead 114 is secured to an anatomical structure of the chest wall 410. The lead anchor 120 may be secured by suturing the lead anchor 120 to an adventitia of intercostal muscle or another anatomical structure within the chest wall 401. The electrode segment 123 extends from the lead anchor 120 to the pericardial membrane, and the lead anchor 120 holds the electrode segment 123 in place within the patient.

At 318, an IMD 11 is implanted within the patient. The IMD 11 may be implanted in a midaxillary region of the chest, the abdomen, the pectoral region, adjacent to the lead anchor 123 in the intercostal space, or at another location within the torso. The IMD 11 is then electrically coupled to the lead 114. After electrically coupling the lead 114 to the IMD 11, the incision at the access opening for the lead and any other incision for the IMD 11 may be closed.

Although FIGS. 8 and 9 describe certain embodiments for implanting a lead using the delivery system 400, it should be understood that other delivery systems may be used, and that one or more operations (or steps) of the method 300 may be modified, replaced, or performed in different stages or at different times. One or more operations may also be added.

Optionally, the pulse generator may be implemented with the hardware, firmware and other components of one or more of implantable medical devices (IMDs) that include neurostimulator devices, implantable leadless monitoring and/or therapy devices, and/or alternative implantable medical devices, although implemented as a subcutaneous implantable medical device. For example, the SIMD may represent a cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No.

9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are all hereby incorporated by reference in their entireties.

Figure 10:
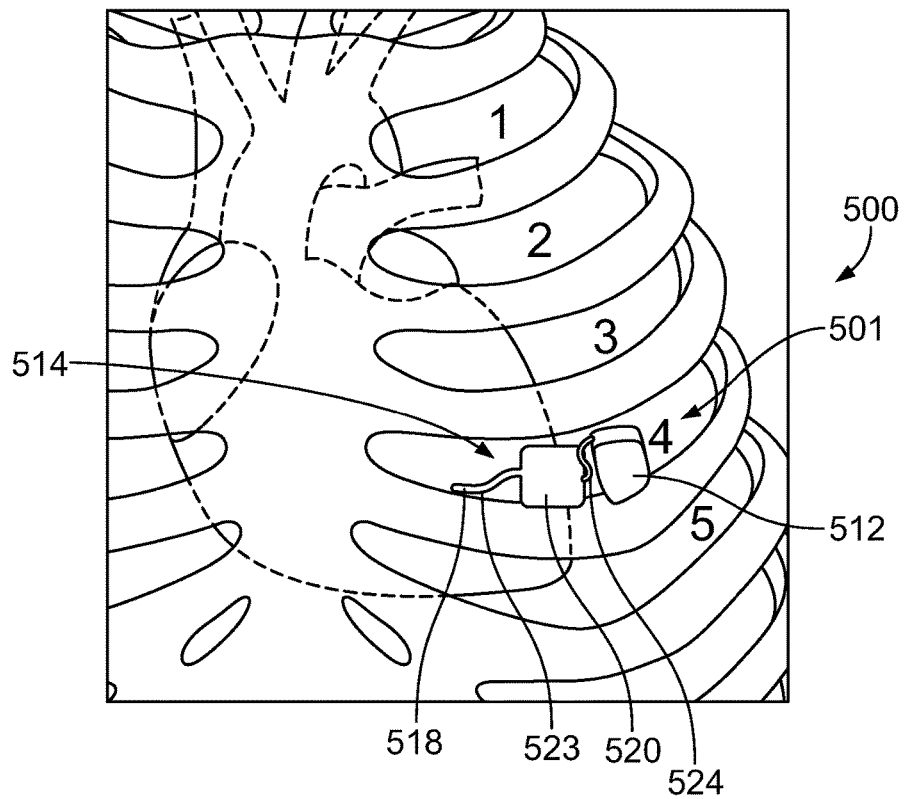
FIG. 10 illustrates an anterior view of a patient and an implantable medical system in the patient in accordance with an embodiment.

FIG. 10 illustrates an anterior view of a patient and an implantable medical system 500 in the patient in accordance with an embodiment. The implantable medical system 500 includes an IMD 501 that has similar and/or identical components as the IMD 11 shown in FIG. 1. The IMD 501 includes a lead 514 and a pulse generator electrically coupled to the lead 514. The lead 514 is shown in more detail in FIG. 11.

Figure 11:
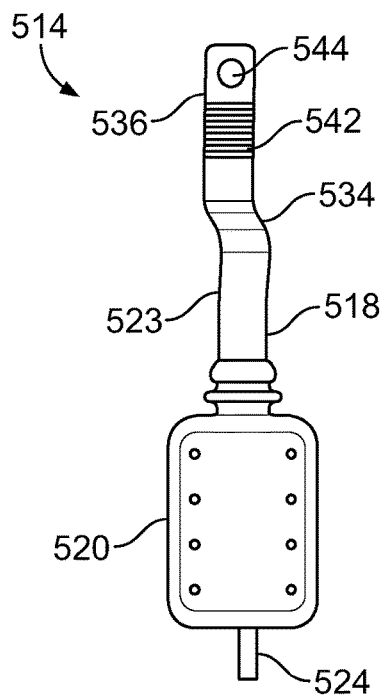
FIG. 11 is a front view of an implantable lead of the implantable medical system shown in FIG. 10, in accordance with an embodiment.

FIG. 11 is a front view of the lead 514 according to an embodiment. The lead 514 includes a lead anchor 520 and a lead body 518. The lead body 518 has an electrode segment 523 and a cable segment 524. The electrode segment 523 differs from the electrode segment 123 of the lead 114 shown in FIGS. 3 and 4 because the electrode segment 523 only has two electrodes, an anode 542 and a cathode 544. The cathode 544 may be similar to the cathode 144 of the lead 114. The anode 542 in the illustrated embodiment is an elliptical coil embedded in the polymeric material of the lead body 518. The coil anode 542 may provide a larger surface area (relative to the patch electrode 142 of the lead 114 in FIG. 4), which may lower impedance for improved pacing efficiency. The lead 514 in FIG. 11 may be designed for sensing of electrical signals and delivering pacing therapy to the heart. In the illustrated embodiment, the lead 514 lacks an electrode for delivering electrical shocks for defibrillation. Similar to the electrode segment 123, the electrode segment 523 includes a transition portion 534 that is a step-down. The electrode segment 523 may also include a contoured portion 536 that is curved to follow a curvature of the pericardial membrane. The curve of the contoured portion 536 extends out of the page in the illustrated orientation.

Referring now back to FIG. 10, the lead 514 and the IMD 512 may be implanted proximate to each other to avoid having to form a second pocket in the patient for accommodating the IMD 512. For example, both the lead 514 and the IMD 512 are disposed in the fourth ($4^{th}$) intercostal space in FIG. 10. Alternatively, the lead 514 and IMD 512 can be located at another intercostal space, such as the fifth ($5^{th}$). The lead 514 may be implanted through the intercostal space into the mediastinum, beyond the chest wall, to enable the electrode segment 523 to extend alongside and optionally mechanically contact the pericardial membrane. The lead anchor 520 and the IMD 512 may be subcutaneously secured to the chest wall. The cable segment 524 of the lead 514 electrically connects the lead 514 to the pulse generator. The IMD 512 is disposed next to the lead anchor 520 in FIG. 10. During the implantation process, the IMD 512 can be inserted into the same access opening as the lead 514 to avoid making two incisions and pockets.

Figure 12:
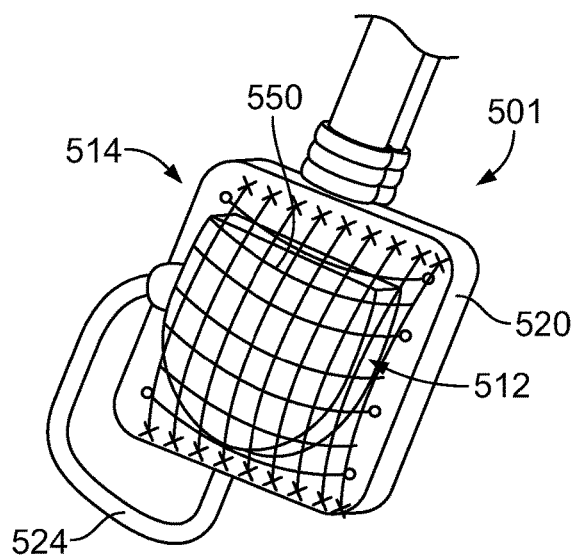
FIG. 12 is a perspective view of a portion of the implantable lead shown in FIGS. 10 and 11 according to an alternative embodiment.

FIG. 12 is a perspective view of a portion of the implantable lead 514 according to an alternative embodiment. In FIG. 12, the IMD 512 is mounted on or to the lead anchor 520. For example, the lead anchor 520 is attached to a dacron pouch 550, and the IMD 512 is held within the dacron pouch 550. The cable segment 524 is short and connects to the IMD 512 in the pouch 550. Alternatively, instead of the pouch 524, the IMD 512 may be mounted to the lead anchor 520 by tying with suture thread, via adhesive, via a mechanical clip or other fastener, or the like. Mounting the IMD 512 on the lead anchor 520 reduces the space within the patient occupied by the IMD 501, relative to having the lead 514 and IMD 512 spaced apart, and avoids having to make multiple pockets.

Figure 13:
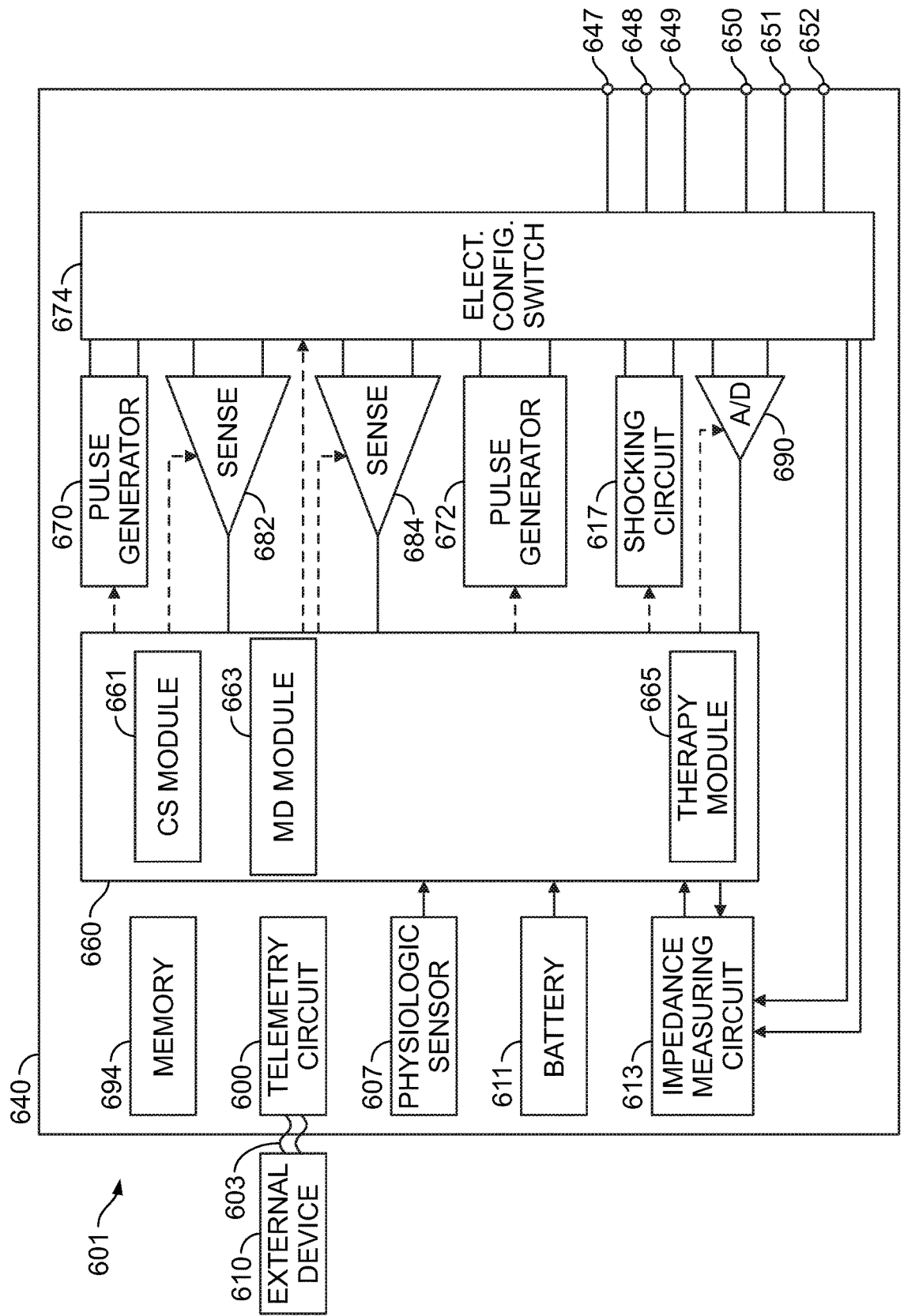
FIG. 13 illustrates a block diagram of an IMD in accordance with an embodiment that is capable of performing stimulation therapy, including cardioversion, defibrillation, and pacing stimulation.

FIG. 13 illustrates a block diagram of an IMD. The IMD is capable of performing stimulation therapy, including cardioversion, defibrillation, and pacing stimulation. The IMD is hereinafter referred to as stimulation device 601. While a particular multi-element device is shown, this is for illustration purposes only. It is understood that the appropriate circuitry could be duplicated, eliminated or disabled in any desired combination to provide a device capable of monitoring impedance and/or cardiac signals, and/or treating the appropriate chamber(s) with cardioversion, defibrillation and pacing stimulation.

The housing 640 for the stimulation device 601 is often referred to as the "canister," "can," "case," or "case electrode" and may be programmably selected to act as the shock electrode and/or as a return electrode for some or all sensing modes. The housing 640 may further be used as a return electrode alone or in combination with one or more other electrodes. The housing 640 further includes a connector (not shown) having a plurality of terminals 647-652. To achieve sensing, pacing, and shocking in connection with desired chambers of the heart, the terminals 647-652 are selectively connected to corresponding combinations of electrodes.

The stimulation device 601 includes a programmable microcontroller 660 that controls the various modes of sensing and stimulation therapy. The microcontroller 660 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 660 includes the ability to process or monitor input signals (data) as controlled by a program code stored in memory. The details of the design and operation of the microcontroller 660 are not critical to the present invention. Rather, any suitable microcontroller 660 may be used.

The microcontroller 660 includes inputs that are configured to collect cardiac signals associated with electrical or mechanical behavior of a heart over at least one cardiac cycle. The cardiac signals may be from the cardiac sensing circuit 682 and representative of electrical behavior of the heart. The circuit 682 may provide separate, combined, composite or difference signals to the microcontroller 660 representative of the sensed signals from the electrodes. Optionally, the cardiac signals may be the output of the A/D circuit 690 that are representative of electrical behavior of the heart. The cardiac signals may be the output of the physiologic sensor 607 that are representative of mechanical behavior.

The microcontroller 660 includes a cardiac signal (CS) module 661, a marker detection (MD) module 663 and a therapy module 665 (among other things). The CS module 661 is configured to analyze cardiac signals. The MD module 663 is configured to analyze signals sensed over the marker sensing channel and identify incoming event markers. The therapy module 665 is configured to modulate, over multiple cardiac cycles, at least one therapy parameter while the stimulation device 601 obtains a collection of at least one CSF indicators associated with different therapy parameters. The therapy module 665 is further configured to adjust a therapy configuration based on, among other things, the cardiac signals and based on the event markers.

The microcontroller 660 further controls a shocking circuit 617 by way of a control signal. The shocking circuit 617 generates stimulating pulses of low (up to 0.5 Joules), moderate (0.5-10 Joules), or high energy (11 to 50 Joules), as controlled by the microcontroller 660. Stimulating pulses may be applied to the patient's heart through at least two shocking electrodes.

One or more pulse generators 670 and 672 generate various types of therapy, such as pacing and ATP stimulation pulses for delivery by desired electrodes. The electrode configuration switch 674 (also referred to as a switch bank) controls which terminals 647-652 are connected to the pulse generators 670, 672, thereby controlling which electrodes receive a therapy. The pulse generators, 670 and 672, may include dedicated, independent pulse generators, multiplexed pulse generators, shared pulse generators or a single common pulse generator. The pulse generators 670 and 672 are controlled by the microcontroller 660 via appropriate control signals to trigger or inhibit stimulation pulses. The microcontroller 660 further includes timing control circuitry which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 674 connects the sensing electronics to the desired terminals 647-652 of corresponding sensing electrodes. For example, a portion of the terminals may be coupled to electrodes configured to define a sensing and/or shocking vector that passes through the left ventricle. The switch 674 may connect terminals to the event marker sensing circuit 684 (which corresponds to the event marker sensing channel) and the microcontroller. The circuit 684 may amplify, filter, digitize and/or otherwise process the sensed signals from the select electrodes.

The switch 674 also connects various combinations of the electrodes to an impedance measuring circuit 613. The impedance measuring circuit 613 includes inputs to collect multiple measured impedances between corresponding multiple combinations of electrodes. For example, the impedance measuring circuit 613 may collect a measured impedance for each or a subset of the active sensing vectors. Optionally, the impedance measuring circuit 613 may measure respiration or minute ventilation; measure thoracic impedance for determining shock thresholds; detects when the device has been implanted; measures stroke volume; and detect the opening of heart valves, etc.

The switch bank 674 includes a plurality of switches for connecting the desired electrodes to the appropriate I/O circuits, thereby providing complete electrode programmability. The switch 674, in response to a control signal from the microcontroller 660, determines the polarity of the stimulation pulses (e.g., unipolar, bipolar, co-bipolar, etc.) by selectively closing the appropriate combination of switches (not specifically shown). The outputs of the cardiac signal and event marker sensing circuits 682 and 684 are connected to the microcontroller 660 which, in turn, is able to trigger or inhibit the pulse generators 670 and 672, respectively. The sensing circuits 682 and 684, in turn, receive control signals from the microcontroller 660 for purposes of controlling the gain, threshold, the polarization charge removal circuitry (not shown), and the timing of any blocking circuitry (not shown).

Cardiac signals are also applied to the inputs of an analog-to-digital (A/D) data acquisition system 690. The data acquisition system 690 is configured to acquire cardiac signals, convert the raw analog data into a digital signal, and store the digital signals for later processing and/or telemetric transmission to an external device 610. The data acquisition system 690 samples cardiac signals across any pair of desired electrodes. The data acquisition system 690 may be coupled to the microcontroller 660, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 660 is further coupled to a memory 694 by a suitable data/address bus 696. The memory 694 stores programmable operating, impedance measurements, impedance derivation and therapy-related parameters used by the microcontroller 660. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart within each respective tier of therapy.

The operating and therapy-related parameters may be non-invasively programmed into the memory 694 through a telemetry circuit 600 in telemetric communication with the external device 610, such as a programmer, trans-telephonic transceiver, or a diagnostic system analyzer. The telemetry circuit 600 is activated by the microcontroller 660 by a control signal. The telemetry circuit 600 advantageously allows data and status information relating to the operation of the device (as contained in the microcontroller 660 or memory 694) to be sent to an external device 101 through an established communication link 603.

The stimulation device 601 may include a physiologic sensor 607 to adjust pacing stimulation rate according to the exercise state of the patient. The physiological sensor 607 may further be used to detect changes in cardiac output, changes in the physiological condition of the heart, or diurnal changes in activity (e.g., detecting sleep and wake states). The battery 611 provides operating power to all of the circuits shown in FIG. 13.

It will be readily understood that the components of the embodiments as generally described and illustrated in the Figures herein, may be arranged and designed in a wide variety of different configurations in addition to the described example embodiments. Thus, the more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

It is to be understood that the above description is intended to be illustrative, and not restrictive. For example, the above-described embodiments (and/or aspects thereof)

may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

What is claimed is:

1. An implantable lead comprising:
a lead body extending between distal and proximal ends, the lead body including an electrode segment configured to be positioned along a pericardial membrane of a heart, the electrode segment including a plurality of electrodes configured to at least one of sense electrical signals from the heart or deliver therapy to the heart;
electrical conductors extending through the lead body between the distal and proximal ends, the electrical conductors configured to electrically couple the electrodes to a pulse generator; and
a lead anchor configured to be secured to an anatomical structure of a chest wall, wherein the electrical conductors extend through the lead anchor, and the electrode segment extends from the lead anchor to the distal end of the lead body, the electrode segment including a transition portion that is configured to extend a depth into a mediastinum and a contoured portion to extend alongside and curve about the pericardial membrane, wherein the lead body is configured to passively fixate the one or more electrodes proximate one or more target treatment areas of the heart.

2. The implantable lead of claim 1, wherein the transition portion is disposed between the lead anchor and the contoured portion and at least one of the transition portion or the contoured portion is configured to bias the electrode segment against the pericardial membrane.

3. The implantable lead of claim 1, wherein the contoured portion of the electrode segment is pre-formed to have a curved shape that follows a contour of the pericardial membrane.

4. The implantable lead of claim 1, wherein the transition portion of the electrode segment defines an S-shaped stepdown configured to change the depth of the implantable lead from the anatomical structure of the chest wall to the pericardial membrane.

5. The implantable lead of claim 1, wherein the lead anchor is a discrete element with respect to the lead body and has an anchor passage, the lead body extending through the anchor passage.

6. The implantable lead of claim 5, wherein the lead body is slidable through the anchor passage to adjust a length that the electrode segment extends from the lead anchor.

7. The implantable lead of claim 5, wherein the lead anchor includes circumferential grooves surrounding the anchor passage, the grooves configured to receive suture threads.

8. The implantable lead of claim 5, wherein the lead anchor has a first flanking portion next to the anchor passage, the first flanking portion defining thru-holes to permit a suture thread to extend through the lead anchor, the thru-holes spaced apart in a row that is parallel to the anchor passage.

9. The implantable lead of claim 1, wherein the lead body and the lead anchor are portions of a monolithic body.

10. The implantable lead of claim 1, wherein the lead anchor has at least one flanking portion that extends along the electrical conductors, wherein an outer dimension of the implantable lead is greater along the at least one flanking portion of the lead anchor than along the electrode segment of the lead body.

11. The implantable lead of claim 10, wherein the at least one flanking portion has thru-holes to permit a suture thread to extend through the lead anchor.

12. The implantable lead of claim 10, wherein the at least one flanking portion includes opposite first and second flanking portions, the lead anchor being paddle-shaped.

13. The implantable lead of claim 1, wherein the plurality of electrodes includes an anode and a cathode for at least one of pacing or bipolar sensing.

14. The implantable lead of claim 13, wherein the plurality of electrodes also includes an embedded elliptical coil for delivering electrical shocks.

15. A method comprising:
inserting an elongated instrument through a chest wall of a patient to create an access opening to an intercostal space within the chest wall, the elongated instrument having a lumen;
tunneling the elongated instrument along the intercostal space to create a passage from the access opening to a mediastinum of the patient;
advancing a guidewire through the lumen of the elongated instrument and into the mediastinum;
removing the elongated instrument;
advancing a dilator over the guidewire and through the intercostal space, thereby increasing a size of the access opening and a size of the passage through the intercostal space;
advancing an implantable lead through the access opening and the passage, the implantable lead having an electrode segment and a lead anchor;
positioning the electrode segment alongside a pericardial membrane of the heart; and
securing the lead anchor to an anatomical structure of the chest wall, wherein the electrode segment extends from the lead anchor to a distal end of the implantable lead, the electrode segment including a transition portion that extends a depth into the mediastinum and a contoured portion that extends alongside and curves to follow a contour of the pericardial membrane, wherein positioning the electrode segment alongside the pericardial membrane and securing the lead anchor to the anatomical structure passively fixates the one or more electrodes proximate one or more target treatment areas of the heart.

16. The method of claim 15, wherein advancing the implantable lead through the access opening and the passage causes the implantable lead to extend through the intercostal space of the chest wall, the transition portion forming an S-shaped step-down which changes the depth of the implantable lead from the chest wall to the pericardial membrane.

17. The method of claim 15, wherein advancing the implantable lead through the access opening and the passage includes rotating the implantable lead from a first orientation in which the contoured portion curves outward toward the chest wall to a second orientation in which the contoured portion curves inward toward the pericardial membrane.

18. The method of claim 15, wherein positioning the electrode segment alongside the pericardial membrane of the heart includes sliding a lead body of the implantable lead through an anchor passage of the lead anchor to adjust a length that the electrode segment extends from the lead anchor.

19. The method of claim 15, further comprising shaping the electrode segment prior to advancing the implantable lead through the access opening.

20. The method of claim 15, wherein positioning the electrode segment alongside the pericardial membrane of the heart includes positioning the electrode segment at least one of along or over the atrioventricular groove.

21. The method of claim 15, wherein securing the lead anchor to the anatomical structure of the chest wall includes suturing the lead anchor to an adventitia of intercostal muscle.

22. The method of claim 15, further comprising implanting a pulse generator adjacent to the lead anchor.

23. An implantable medical system comprising:
a pulse generator configured to be positioned within a patient, the pulse generator having a housing that includes an electronics module configured to at least one of analyze electrical signals of a heart or generate electrical signals for delivering therapy to the heart; and
a lead including a lead body extending between distal and proximal ends, the lead body including an electrode segment including a plurality of electrodes configured to at least one of sense the electrical signals from the heart or deliver the therapy to the heart, wherein the lead also includes electrical conductors and a lead anchor, the electrical conductors extending through the lead body and electrically coupling the electrodes to the pulse generator, the lead anchor configured to be secured to an anatomical structure of a chest wall, wherein the electrical conductors extend through the lead anchor, and the electrode segment extends from the lead anchor to the distal end of the lead body, the electrode segment including a transition portion that is configured to extend a depth into a mediastinum and a contoured portion configured to extend alongside and curve about a pericardial membrane of the heart, wherein the transition portion is disposed between the lead anchor and the contoured portion and defines an S-shaped step-down configured to change the depth of the implantable lead from the anatomical structure of the chest wall to the pericardial membrane.

* * * * *